(12) United States Patent
Kushida et al.

(10) Patent No.: US 11,098,341 B2
(45) Date of Patent: Aug. 24, 2021

(54) METHOD FOR DETERMINING WHETHER OR NOT TEST SAMPLE CONTAINS PHYTOPATHOGENIC FUNGUS

(71) Applicant: Panasonic Intellectual Property Management Co., Ltd., Osaka (JP)

(72) Inventors: Yuki Kushida, Kyoto (JP); Yoshitsugu Uriu, Osaka (JP); Yosifumi Kariatumari, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/547,655

(22) Filed: Aug. 22, 2019

(65) Prior Publication Data

US 2019/0376107 A1 Dec. 12, 2019

Related U.S. Application Data

(63) Continuation of application No. PCT/JP2018/014064, filed on Apr. 2, 2018.

(30) Foreign Application Priority Data

Apr. 28, 2017 (JP) .............................. JP2017-089340

(51) Int. Cl.
| | |
|---|---|
| *G01N 21/17* | (2006.01) |
| *G01N 21/78* | (2006.01) |
| *G01N 33/569* | (2006.01) |
| *C12Q 1/04* | (2006.01) |
| *G01N 1/28* | (2006.01) |

(52) U.S. Cl.
CPC .............. *C12Q 1/04* (2013.01); *G01N 1/2813* (2013.01); *G01N 21/17* (2013.01); *G01N 21/78* (2013.01); *G01N 33/56961* (2013.01)

(58) Field of Classification Search
CPC ........ C12Q 1/04; G01N 1/2813; G01N 21/17; G01N 21/78; G01N 33/56961
USPC ....................................... 435/40.5
See application file for complete search history.

(56) References Cited

U.S. PATENT DOCUMENTS

| 9,689,020 B2 | 6/2017 | Uriu | |
|---|---|---|---|
| 2004/0033555 A1* | 2/2004 | Anderson | ............... C12Q 1/18 435/34 |
| 2019/0048388 A1 | 2/2019 | Yamaguchi et al. | |

FOREIGN PATENT DOCUMENTS

| EP | 3128001 | 2/2017 |
|---|---|---|
| EP | 3438277 | 2/2019 |
| EP | 3575405 | 12/2019 |
| JP | 2005-287337 | 10/2005 |
| JP | 2017-029131 | 2/2017 |
| WO | 2018/011835 | 1/2018 |

OTHER PUBLICATIONS

The Extended European Search Report dated Mar. 17, 2020 for the related European Patent Application No. 18790194.7.
International Search Report of PCT application No. PCT/JP2018/014064 dated Jul. 3, 2018.
Paul F. Morris et al., "Chemotropic and Contact Responses of Phytophthora sojae Hyphae to Soybean Isoflavonoids and Artificial Substrates", Plant Physiol. (1998) 117: 1171-1178, Aug. 1, 1998.

* cited by examiner

*Primary Examiner* — Jennifer M. H. Tichy
(74) *Attorney, Agent, or Firm* — McDermott Will and Emery LLP

(57) ABSTRACT

A method for determining whether a test sample contains a phytopathogenic fungus, which includes (a) putting the test sample on a front surface of a substrate having a through hole; the substrate having a cellulose film on the back surface thereof; the through hole has a cross-sectional area of not less than 7.065 square micrometers and not more than 19.625 square micrometers; and the cellulose film has a thickness of not less than 0.5 micrometers and not more than 3.7 micrometers; (b) leaving the test sample at rest after the step (a); (c) irradiating the cellulose film with ultraviolet light after the step (b); (d) bringing a back surface of the cellulose film into contact with a fungus color reaction reagent after the step (c); and (e) determining that the test sample contains the phytopathogenic fungus, if a color is given to the fungus color reaction reagent.

15 Claims, 9 Drawing Sheets

METHOD FOR DETERMINING WHETHER OR NOT TEST SAMPLE CONTAINS PHYTOPATHOGENIC FUNGUS

BACKGROUND

1. Technical Field

The present invention relates to a method for determining whether or not a test sample contains a phytopathogenic fungus.

2. Description of the Related Art

Patent Literature 1 discloses a method for counting the number of mold cells. FIG. 10 shows a cross-sectional view of a microporous membrane supporting material which is used for the method disclosed in Patent Literature 1. The method for counting the number of mold cells disclosed in Patent Literature 1 provides a method for counting the number of mold cells in a specimen by the culture for a short time and capable of accurately counting the cell number. In the method for counting the number of mold cells disclosed in Patent Literature 1, the extended multiple pseudomycelia of a mold cell 13 cultured by a liquid culture or a mold cell 13 cultured on a microporous membrane 1 of a microporous membrane supporting material 4 are photographed and the shape, area and luminous intensity are recognized and analyzed by an image analytic means 10. The number of the mold cells 13 can be counted by the culture for a short time. The microporous membrane 1 is interposed between a pressing ring 2 and a base 3.

Non-patent Literature 1 discloses that pseudohyphae of *Phytophthora sojae*, which is one kind of phytopathogenic pythiums, penetrate a PET film having pores each having a diameter of 3 micrometers.

Patent Literature 2 discloses a method for determining whether or not a test sample contains a phytopathogenic oomycete.

CITATION LIST

Patent Literature

Patent Literature 1: Japanese Patent Application laid-open Publication No. 2005-287337
Patent Literature 2: Japanese Patent Application laid-open Publication No. 2017-029131

Non-Patent Literature

Non-patent Literature 1: Paul F. Morris. et. al. "Chemotropic and Contact Responses of *Phytophthora sojae* Hyphae to Soybean Isoflavonoids and Artificial Substrates", Plant Physiol. (1998) 117: 1171-1178

SUMMARY

An object of the present invention is to provide a method for determining whether or not a test sample contains a phytopathogenic fungi selectively from two kinds of fungi of a phytopathogenic fungus and a non-phytopathogenic fungus.

The present invention provides a method for determining whether or not a test sample contains a phytopathogenic fungus. The method comprises:

(a) putting the test sample on a front surface of a cellulose film;
wherein
the substrate comprises a cellulose film on the back surface thereof;
the through hole of the substrate has a cross-sectional area of not less than 7.065 square micrometers and not more than 19.625 square micrometers;
the cellulose film has no through hole; and
the cellulose film has a thickness of not less than 0.5 micrometers and not more than 3.7 micrometers;
(b) leaving the test sample at rest after the step (a);
(c) irradiating the cellulose film with ultraviolet light using an ultraviolet light source provided so as to face the front surface of the cellulose film after the step (b);
(d) bringing a back surface of the cellulose film into contact with a fungus color reaction reagent after the step (c); and
(e) determining that the test sample contains the phytopathogenic fungus, if a color is given to the fungus color reaction reagent.

The present invention provides a method for determining whether or not a test sample contains a phytopathogenic fungi selectively from two kinds of fungi of a phytopathogenic fungus and a non-phytopathogenic fungus.

DETAILED DESCRIPTION OF THE EMBODIMENT

Figure 1:
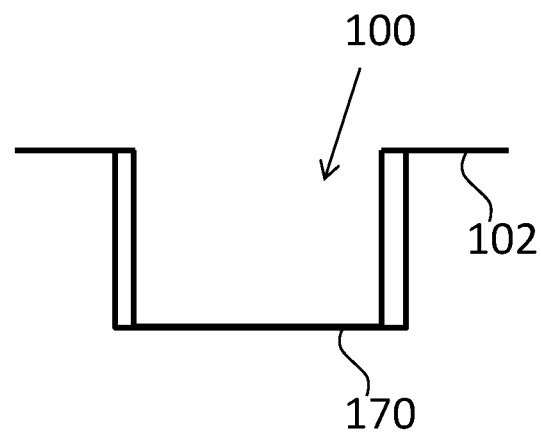
FIG. 1 shows a cross-sectional view of a first container 100.

First, the term "fungus" used in the instant specification will be described. The term "fungus" includes mycete and oomycete. Fungi are roughly divided into a phytopathogenic fungus and a non-phytopathogenic fungus. For example, the phytopathogenic mycete includes a *Fusarium* genus, a *Colletotrichum* genus, a *Botrytis* genus, a *Passalora* genus, or a *Pseudocercospora* genus. An example of the phytopathogenic mycete is *Fusarium avenaceum, Colletotrichum*

*gloeosporioides*, *Botrytis cinerea*, *Passalora fulva*, or *Pseudocercospora fuligena*. These phytopathogenic fungi cause root rot disease, blast, anthrax, or gray mold. These phytopathogenic fungi kill the plant. An example of the non-phytopathogenic fungus is *Saccharomyces cerevisiae*, *Penicillium chysogeum* or *Aspergillus oryzae*.

The term "phytopathogenic" means to have pathogenicity to plants. The term "non-phytopathogenic" means not to have pathogenicity to plants. Even if a fungus has pathogenicity, however, if the fungus has no pathogenicity to plants, the fungus is non-phytopathogenic. In other words, if a fungus does not have adverse effects on plants, the fungus is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings. Japanese Patent Publication No: 6167309, U.S. Pat. No. 9,695,459, European Patent Publication No.: 3128001, Japanese Patent Publication No: 6167310, U.S. Pat. No. 9,689,020, European Patent Publication No. 3128002, International Patent Application No: PCT/JP2016/004417, and International Patent Application No: PCT/JP2017/008407 are incorporated herein by reference.

(Step (a))

In the step (a), a test sample is put on a front surface of a substrate 170 comprising through holes 172. A cellulose film 104 is adhered to a back surface 170b of the substrate 170. In other words, a front surface 104a of the cellulose film 104 is in contact with the back surface 170b of the substrate 170. The front surface 104a means the upper surface of the cellulose film 104.

In particular, as shown in FIG. 1, a container 100 is prepared. It is desirable that the container 100 comprises a flange 102 at the upper end thereof. The bottom surface of the container 100 is formed of the substrate 170.

Figure 2:
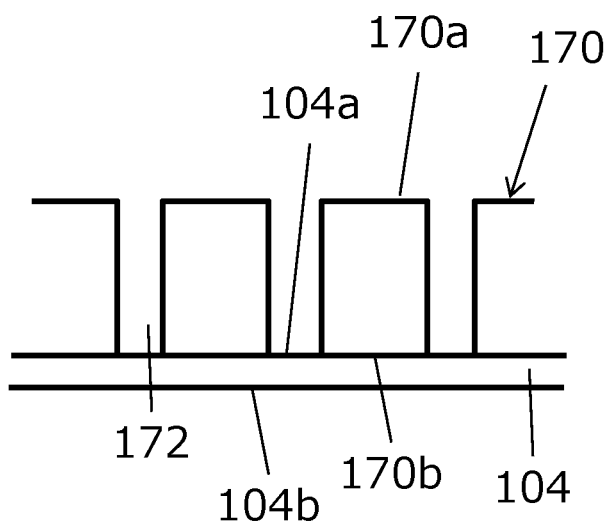
FIG. 2 shows a cross-sectional view of a substrate 170 comprising a cellulose film 104 on the back surface thereof.

As shown in FIG. 2, the substrate 170 comprises the cellulose film 104 on the back surface 170b thereof. The substrate 170 comprises a through hole 172 which penetrates from the front surface 170a to the back surface 170b of the substrate 170. The through hole 172 has a diameter of not less than 3 micrometers and not more than 5 micrometers. See U.S. patent application Ser. No. 16/162,467 and U.S. patent application Ser. No. 16/410,362. In other words, the through hole 172 has a cross-sectional diameter of not less than 7.065 square micrometers and not more than 19.625 square micrometers. See U.S. patent application Ser. No. 16/162,467 and U.S. patent application Ser. No. 16/410,362. Unlike the substrate 170, note that the cellulose film 104 has no through hole.

Figure 3:
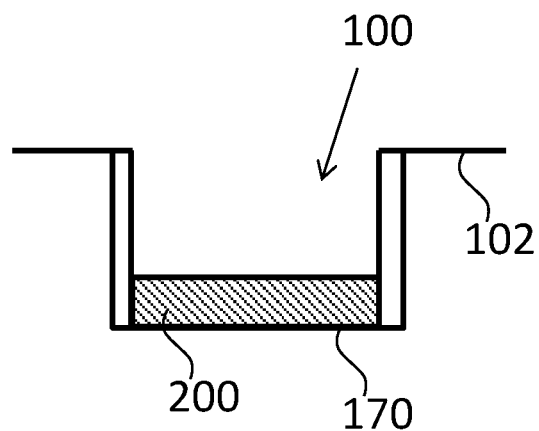
FIG. 3 shows a cross-sectional view of the first container 100 to which a test sample has been supplied.
Figure 4:
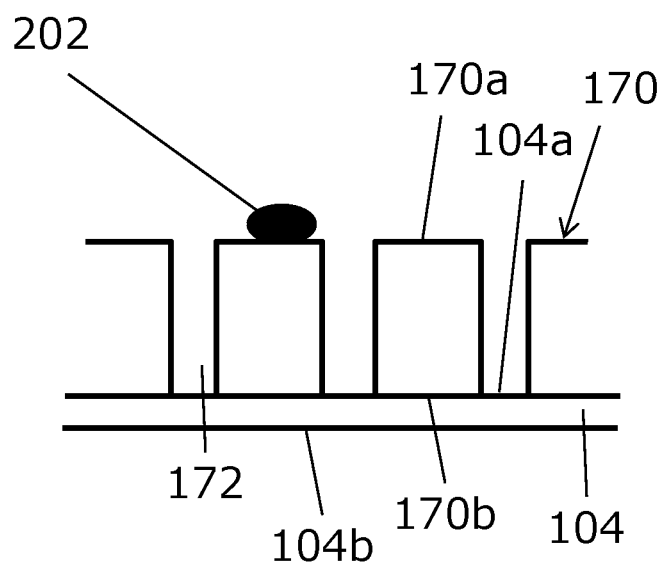
FIG. 4 shows a cross-sectional view of the substrate 170 having a front surface on which a phytopathogenic fungus has been put.

As shown in FIG. 3, a test sample 200 is supplied to the inside of this container 100. In this way, the test sample 200 is put on the front surface 170a of the substrate 170. When the test sample 200 contains a phytopathogenic fungus 202, the phytopathogenic fungus 202 is put on the front surface 170a of the substrate 170, as shown in FIG. 4.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used for washing a plant, a liquid extracted from a plant, a liquid used for washing an agricultural material, or a liquid used for washing clothing or shoes of a worker.

(Step (b))

In the step (b), the test sample 200 is left at rest for a certain incubation time after the step (a). Desirably, the test sample 200 is left at rest for approximately 4-150 hours (more desirably, 24-120 hours). In this way, the fungus is incubated. In other words, the incubation time is approximately 4-150 hours (more desirably, 24-120 hours). Hereinafter, the importance of the thickness of the cellulose film 104 and the size of the through hole 172 will be described.

Figure 5A:
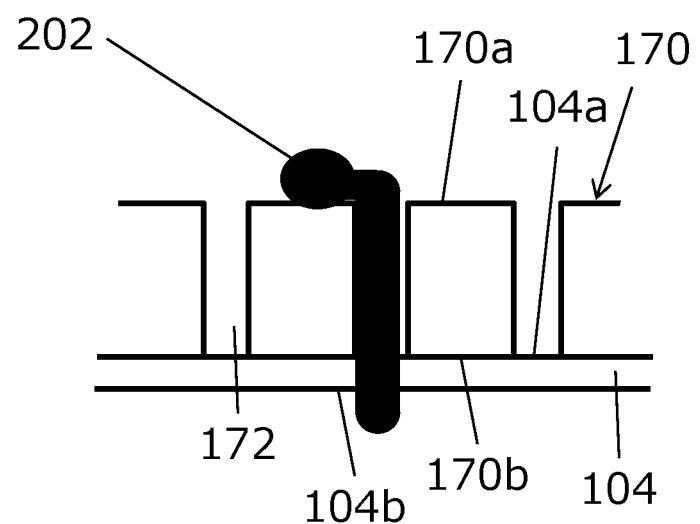
FIG. 5A is a cross-sectional view showing a state where the phytopathogenic fungus has penetrated a through-hole 172 and the cellulose film 104.

In the step (b), various fungi contained in the test sample 200 are grown. As demonstrated in U.S. Pat. Nos. 9,695,459, 9,689,020, U.S. patent application Ser. No. 16/162,467, and U.S. patent application Ser. No. 16/410,362, if the following requirement (I) is satisfied, the phytopathogenic fungus 202 grows up so as to penetrate the cellulose film 104, as shown in FIG. 5A. As a result, the phytopathogenic fungus 202 appears on a back surface 104b of the cellulose film 104.

Requirement (I): The cellulose film 104 has a thickness of not less than 0.5 micrometers and not more than 3.7 micrometers.

If the above requirement (I) is satisfied, the non-phytopathogenic fungus hardly penetrates the cellulose film 104. For this reason, the non-phytopathogenic fungus hardly appears on the back surface 104b of the cellulose film 104. On the other hand, the phytopathogenic fungus 202 appears on the back surface 104b selectively. As just described, the phytopathogenic fungus 202 appears outside of the container 100 selectively. The back surface 104b means the lower surface of the cellulose film 104.

In case where the cellulose film 104 has a thickness of more than 3.7 micrometers, neither the non-phytopathogenic fungus nor the phytopathogenic fungus penetrates the cellulose film 104. Therefore, in case where the cellulose film 104 has a thickness of more than 3.7 micrometers, the selectivity is lost. When the cellulose film 104 has a thickness of less than 0.5 micrometers (including a case where the cellulose film 104 is not provided), not only the phytopathogenic fungus but also the non-phytopathogenic fungus penetrates the cellulose film 104 (or are found on the back surface 170b of the substrate 170). Therefore, the selectivity is lost when the cellulose film 104 has a thickness of less than 0.5 micrometers.

In case where the through hole 172 has a cross-sectional area of less than 7.065 square micrometers (namely, a diameter of less than 3 micrometers), it is hard for not only the non-phytopathogenic fungus but also the phytopathogenic fungus to penetrate the cellulose film 104. On the other hand, the through hole 172 has a cross-sectional area of more than 19.625 square micrometers (namely, a diameter of more than 5 micrometers), the number of hyphae which penetrated cellulose film 104 tends to be lowered, compared to the case where the through hole 172 has a cross-sectional area of 19.625 square micrometers (namely, a diameter of 5 micrometers).

The cellulose film 104 is stretched taut on the back surface 170b of the substrate 170. In other words, the substrate 170 for supporting the cellulose film 104 is used.

As shown in FIG. 2, the substrate 170 has a plurality of through holes 172. The thickness of the substrate 170 is not limited; however, as one example, it is desirable that the substrate 170 has a thickness of not less than 1 micrometer and not more than 500 micrometers. The cellulose film 104 is significantly thin. However, if the cellulose film 104 is arranged on the substrate 170, it is easy to handle the cellulose film 104.

A culture medium may be supplied to the test sample 200 to accelerate the incubation of the fungus. In particular, a culture medium may be supplied to the inside of the container 100 containing the test sample 200. It is desirable that the culture medium is liquid. The culture medium may be supplied in the step (b). Alternatively, the culture medium may be supplied prior to the step (b). In other words, the culture medium may be supplied in the step (a). The culture medium may be supplied to the inside of the container 100 prior to the step (a).

Figure 6:
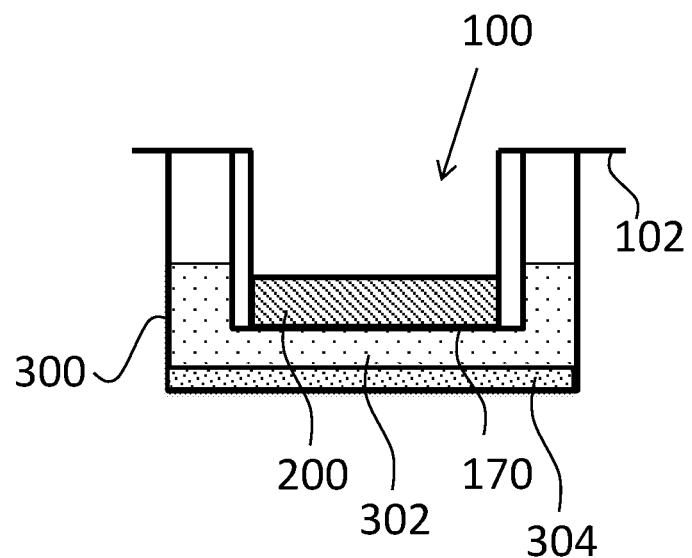
FIG. 6 shows a cross-sectional view of one example of a method for accelerating the incubation of the fungus.

FIG. 6 shows another method for accelerating the incubation of the fungus. As shown in FIG. 6, it is desirable that the back surface 104b of the cellulose film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104b of the cellulose film 104 and the bottom surface of the second container 300.

Alternatively, after the first container 100 is stacked on the second container 300, the liquid culture medium 302 may be supplied between the back surface 104b of the cellulose film 104 and the bottom surface of the second container 300.

In place of the liquid culture medium 302, a viscous solid culture medium may also be used. As shown in FIG. 6, both of a solid culture medium 304 and the liquid culture medium 302 may be used. In this case, the liquid culture medium 302 is sandwiched between the solid culture medium 304 and the cellulose film 104. As shown in FIG. 5A, the incubation of the phytopathogenic fungus which has appeared on the back surface 104b is accelerated by at least one of the liquid culture medium 302 and the solid culture medium 304.

(Step (c))

Figure 5B:
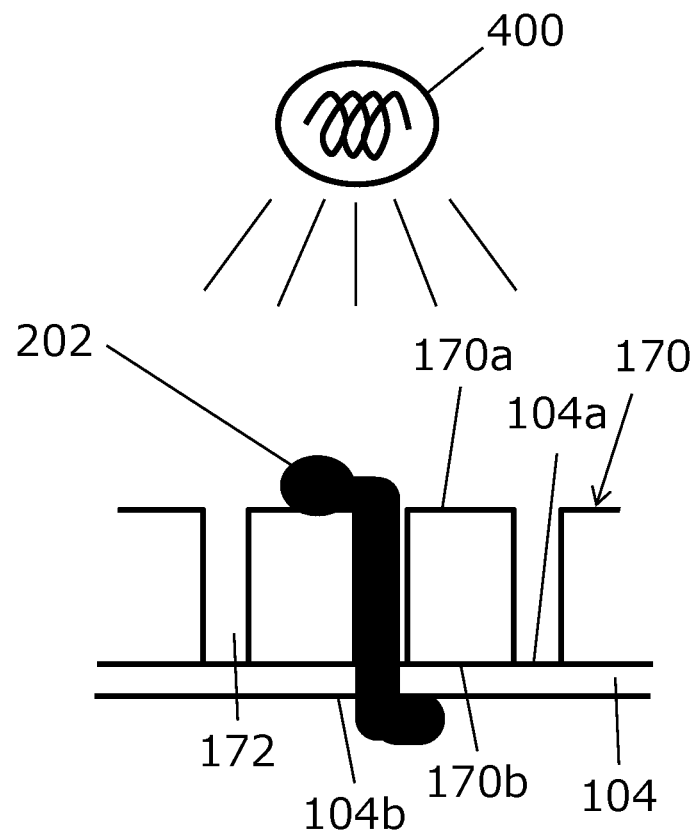
FIG. 5B is a cross-sectional view in a step (c).

In the step (c), as shown in FIG. 5B, the cellulose film 104 is irradiated with ultraviolet light using a ultraviolet light source 400 provided above the front surface 104a of the cellulose film 104 after the step (b).

Figure 5C:
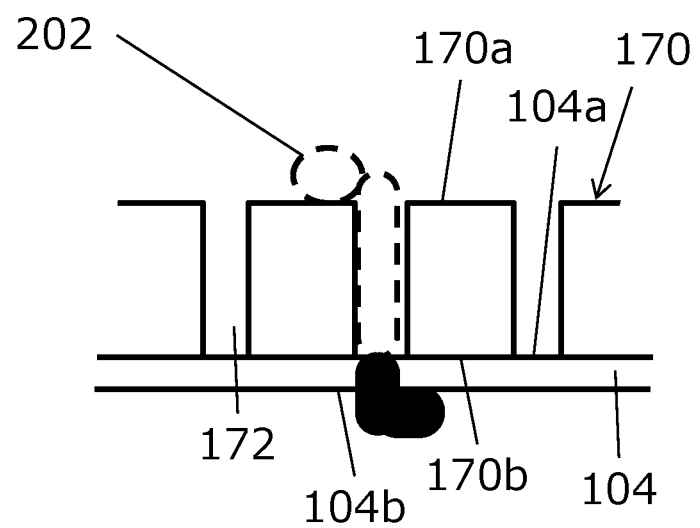
FIG. 5C is a cross-sectional view after the step (c).

Due to sterilization by ultraviolet radiation, as shown in FIG. 5C, a part of the phytopathogenic fungus 202 located on the front surface 104a of the cellulose film 104 is killed. See the dashed line included in FIG. 5C. Similarly, a part of the non-phytopathogenic fungus located on the front surface 104a of the cellulose film 104 is also killed. On the other hand, since the cellulose film 104 shields ultraviolet light, a part of the phytopathogenic fungus 202 located on the back surface 104b of the cellulose film 104 (namely, the part of the phytopathogenic fungus 202 which has penetrated the cellulose film 104) remains alive. The substrate 170 also shields ultraviolet light.

The intensity and the irradiation time of the ultraviolet light can be selected properly by a skilled person who has read the instant specification. Since ultraviolet light having too strong an intensity is not shielded sufficiently by the cellulose film 104 and the substrate 170, it also kills the part of the phytopathogenic fungus 202 located on the back surface 104b of the cellulose film 104. As a result, the selectivity of the fungi is lost. Too long an irradiation time of the ultraviolet light also causes a similar problem.

(Step (d))

In the step (d), the back surface 104b of the cellulose film 104 is brought into contact with a fungus color reaction reagent after the step (c). In this way, the part of the phytopathogenic fungus 202 which has appeared on the back surface 104b of the cellulose film 104 (See FIG. 5C) gives a color to the fungus color reaction reagent. A living fungus reacts with the fungus color reaction reagent to give a color to the fungus color reaction reagent. On the other hand, a dead fungus does not react with the fungus color reaction reagent. As a result, the dead fungus does not give a color to the fungus color reaction reagent. The fungus color reaction reagent is usually soluble in water.

Theoretically, since the first container 100 is separated from the second container 300 by the cellulose film 104, the fungus color reaction reagent does not spread into the first container 100. For this reason, the non-phytopathogenic fungus contained in the first container 100 does not give a color to the fungus color reaction reagent.

However, actually, the fungus color reaction reagent may be spread into the inside of the first container 100 through a small interspace formed around the phytopathogenic fungus 202 which has penetrated the cellulose film 104. In addition, since the fungus color reaction reagent is usually soluble in water, the fungus color reaction reagent may be spread onto the front surface 104a of the cellulose film 104 through the inside of the cellulose film 104.

For this reason, the part of the phytopathogenic fungus 202 located on the front surface 104a of the cellulose film 104 also gives a color to the fungus color reaction reagent. Furthermore, the non-phytopathogenic fungus (not shown) located on the front surface 104a of the cellulose film 104 also gives a color to the fungus color reaction reagent. Therefore, the selectivity of the fungi is lost.

On the other hand, as shown in FIG. 5C, due to the irradiation of the ultraviolet light, the phytopathogenic fungus 202 and the non-phytopathogenic fungus (not shown) are killed on the front surface 104a of the cellulose film 104. However, the part of the phytopathogenic fungus 202 is left alive on the back surface 104b of the cellulose film 104. The part of the phytopathogenic fungus 202 left alive on the back surface 104b gives a color to the fungus color reaction reagent. Needless to say, since the non-phytopathogenic fungus does not penetrate the cellulose film 104, the non-phytopathogenic fungus does not give a color to the fungus color reaction reagent. In this way, in the present embodiment, the part of the phytopathogenic fungus 202 which has penetrated the cellulose film 104 gives a color to the fungus color reaction reagent selectively.

An example of the fungus color reaction reagent is a chemical material having the following chemical structure [Chem. 1]. The chemical material is referred to as "WST-8".

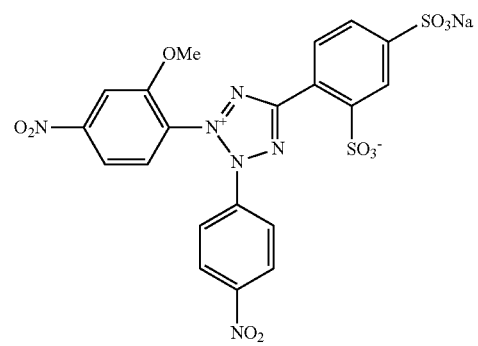

[Chem. 1]

Figure 7:
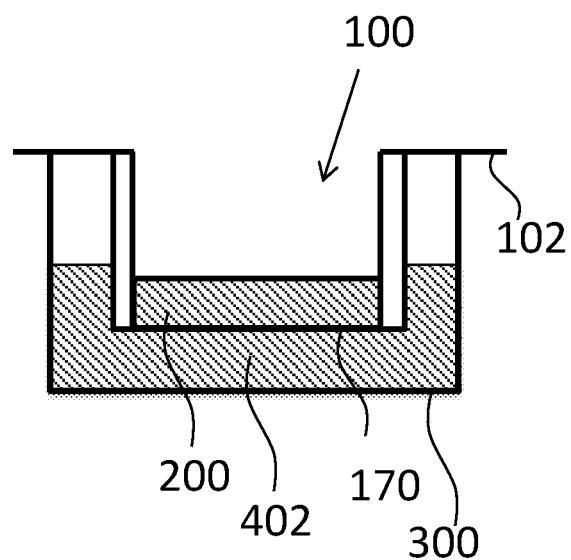
FIG. 7 shows a cross-sectional view, subsequently to FIG. 6, of one example of a method for accelerating the incubation of the fungus.
Figure 8:
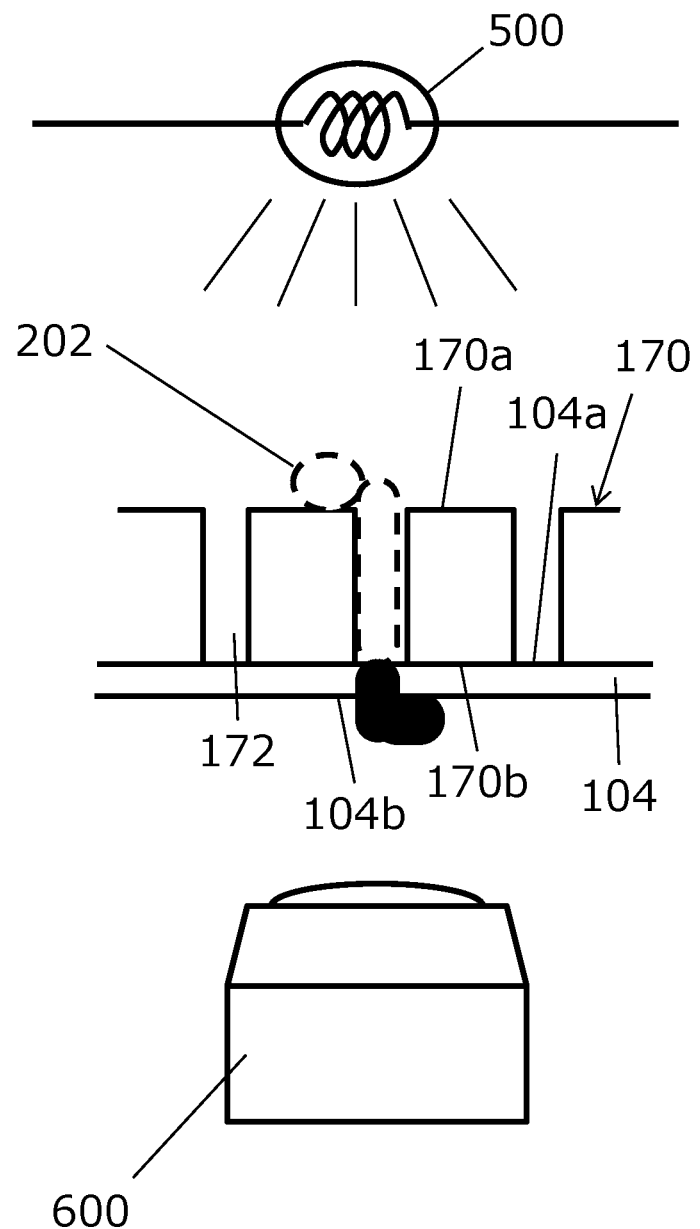
FIG. 8 is a cross-sectional view showing how to observe the fungus from the back surface of the cellulose film 104.
Figure 9:
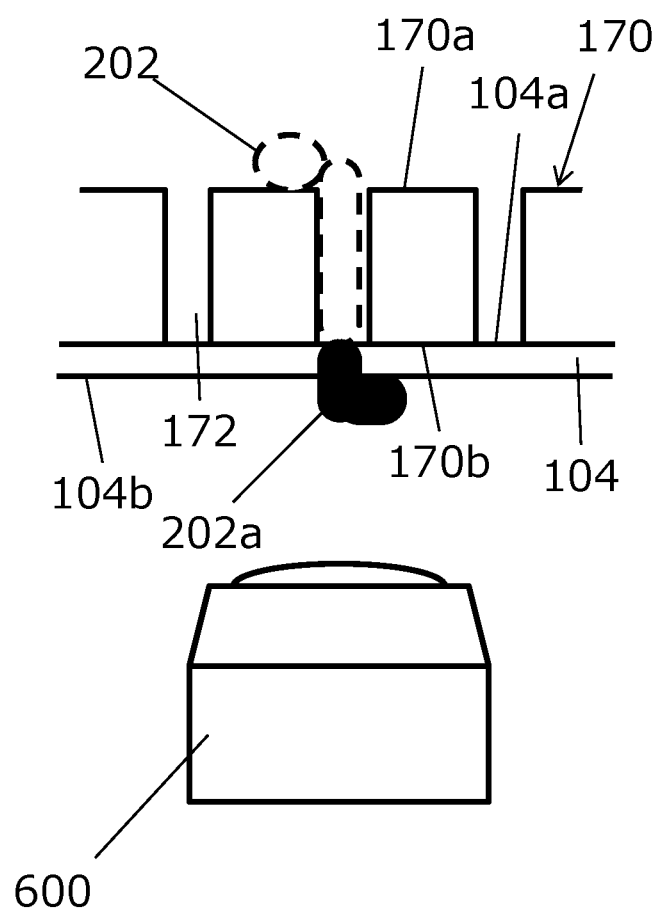
FIG. 9 is a cross-sectional view showing how to observe the fungus from the back surface of the cellulose film 104.
Figure 10:
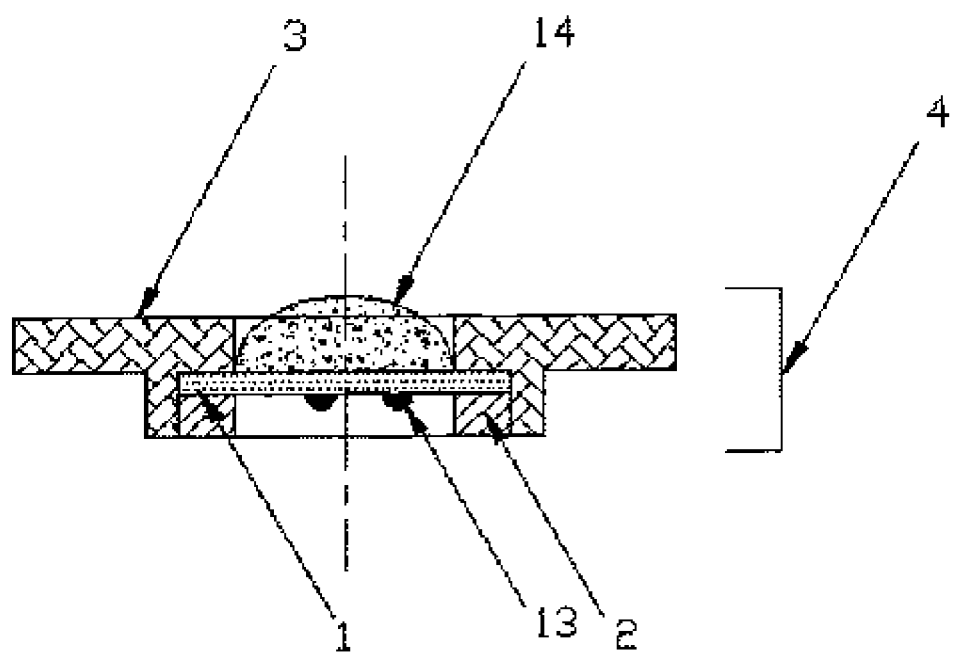
FIG. 10 shows a cross-sectional view of the microporous membrane supporting material used for the method for counting the number of mold cells disclosed in Patent Literature 1.

In particular, after the step (c), the liquid culture medium 302 and the solid culture medium 304 are removed from the second container 300. Then, the fungus color reaction reagent is added to the inside of the second container 300. Then, as shown in FIG. 7, the first container 100 is stacked on the second container 300 having the fungus color reaction reagent therein. Alternatively, a solution 402 containing the fungus color reaction reagent may be supplied between the back surface 104b of the cellulose film 104 and the bottom surface of the second container 300 after the first container 100 is stacked on the second container 300. Alternatively, since a liquid can permeate the cellulose film 104, the solution 402 containing the fungus color reaction reagent may be supplied into the first container 100.

(Step (e))

In the step (e), it is determined that the test sample contains phytopathogenic fungus, if a color is given to the fungus color reaction reagent in the step (d).

The present invention includes a device used for conducting the method for determining selectively whether or not the above-mentioned phytopathogenic fungus is contained.

The device according to the present invention comprises, at least, a substrate and a cellulose film. The substrate comprises a through hole having a cross-sectional area of not less than 7.065 square micrometers and not more than 19.625 square micrometers, in other words, a diameter of not less than 3 micrometers and not more than 5 micrometers. The substrate may be a container in which the bottom thereof is composed of the substrate and a flange is comprised. The cellulose film is comprised on one surface of the substrate and has a thickness of not less than 0.5 micrometers and not more than 3.7 micrometers. The cellulose film does not have a through hole.

The device according to the present invention may comprise a medium for accelerating the culture of the fungus or the fungus color reaction reagent. In addition, the device according to the present invention may comprise an ultraviolet light source for irradiation the cellulose film with ultraviolet light, an optical sensor for optically detecting the color given to the fungus color reaction reagent, or a display element for displaying results of the detection.

As long as the effect of the present invention is prevented, another layer may be interposed between the cellulose film and the substrate. However, it is desirable that the cellulose film is in contact with the substrate. In other words, as long as the effect of the present invention is prevented, the cellulose film does not have to be in contact with the substrate. In this case, the cellulose film may be located on the substrate in such a manner that another layer is interposed between the cellulose film and the substrate. However, as described above, it is desirable that the cellulose film is located on the substrate so as to be in contact with the substrate.

EXAMPLES

The present invention will be described in more detail with reference to the following examples.

(Preparation of Culture Medium)

First, the present inventors dissolved iron (III) sulfate (0.56 mM), zinc nitrate (1.53 mM), and manganese (II) sulfate (1.1 mM) to pure water (1 liter) to prepare an aqueous solution. Then, the present inventors added pure water (1 liter), lactose (37.5 grams, purchased from SIGMA-ALDRICH), casein hydrate (3.0 grams, purchased from Difco), potassium dihydrogen phosphate (1.0 gram, purchased from Wako Pure Chemical Industries, Ltd.), and magnesium sulfate (0.5 grams, purchased from Wako Pure Chemical Industries, Ltd.) to the aqueous solution (2 mL) to dissolve the mixture. The present inventors sterilized the mixture with an autoclave apparatus. The mixture had a pH of 6.0. The present inventors diluted the mixture ten-fold with pure water to obtain a culture medium. Hereinafter, the thus-obtained culture medium is referred to as "10% LCH culture medium".

(Preparation of WST Reaction Liquid)

The present inventors dissolved Duroquinone (purchased from Tokyo Chemical Industry Co., Ltd., CAS No: 527-17-3) with ethanol (purchased from Wako Pure Chemical Industries, Ltd.) to obtain a Duroquinone ethanol solution (50 mM). Apart from this, the present inventors dissolved 2-cyclohexylaminoethanesulfonic Acid (purchased from Tokyo Chemical Industry Co., Ltd., CAS No: 103-47-9, hereinafter referred to as "Chem") with pure water to obtain a Chem solution (100 mM). The present inventors added drops of an NaOH aqueous solution (1M, purchased from Wako Pure Chemical Industries, Ltd.) to adjust a pH of the Chem solution to 9.5.

The present inventors mixed reagents shown in the following Table 1 to obtain a WST reaction liquid.

TABLE 1

| Name of Reagent | Volume ratio |
| --- | --- |
| 10% LCH Culture Medium | 170 |
| WST-8 Solution | 9 |
| Duroquinone ethanol solution (50 mM) | 1 |
| Chem solution (100 mM) | 20 |

The WST-8 solution was included in a product purchased from Dojindo Laboratories as a trade name of WST-8 Microbial Viability Assay Kit-WST. WST-8 has the chemical structure mentioned above as "[Chem. 1]".

(Incubation of *Colletotrichum gloeosporioides*)

*Colletotrichum gloeosporioides*, one of phytopathogenic fungi, was inoculated on a potato dextrose agar culture medium. Then, the culture medium was left at rest at a temperature of 25 degrees Celsius for one week. *Colletotrichum gloeosporioides* was given by an associate professor, Mr. Shimizu, who belongs to Graduate School of Applied Biological Sciences and Faculty of Applied Biological Sciences, Gifu University.

Then, a part including ends of hyphae was cut together with the culture medium at a size of 1 centimeter×1 centimeter. The cut part was immersed in the 10% LCH culture medium disposed on a 12-well plate. Each of the pure water has a volume of 1 milliliter.

The water contained in the 12-well plate was observed using an optical microscope. As a result, the present inventors confirmed that spores of *Colletotrichum gloeosporioides* were released in the water disposed on the 12-well plate. In this way, an aqueous solution containing *Colletotrichum gloeosporioides* was provided. Hereinafter, this aqueous solution is referred to as "phytopathogenic fungus aqueous solution".

(Experiment 1)

The experiment 1 is composed of inventive examples 1A-1D.

Inventive Example 1A

The first container 100 shown in FIG. 1 was prepared as below.

First, cellulose (provided from SIGMA-ALDRICH Co. LLC, trade name: Avicel PH-101) was dissolved in an ionic liquid to prepare a cellulose solution having a concentration of 1%. The ionic liquid was 1-butyl-3-methyl imidazolium chloride (provided from SIGMA-ALDRICH Co. LLC).

The cellulose solution was warmed to 60 degrees Celsius. Then, the cellulose solution was applied by a spin coat method for thirty seconds at a rotation speed of 2,000 rpm onto a back surface of a container having a polyethylene terephthalate film on the bottom surface thereof (provided from Millipore company, trade name: Millicell PISP 12R 48). The polyethylene terephthalate film served as the substrate 170. The polyethylene terephthalate film randomly had a plurality of through holes 172 each having a diameter of three micrometers. In this way, the cellulose film 104 having a thickness of 0.5 micrometers was formed on the back surface of the polyethylene terephthalate film. According to Merck KGaA, the diameter of the through-hole 172 may have a margin of error of approximately ±10%.

The container was left at rest in ethanol at room temperature for 12 hours. In this way, 1-butyl-3-methyl imidazolium chloride was replaced with ethanol. In other words, 1-butyl-3-methyl imidazolium chloride was removed from the cellulose film 104.

Finally, the container was dried in a vacuum desiccator. In this way, the first container 100 shown in FIG. 1 was obtained. In FIG. 1, note that the polyethylene terephthalate film serving as the substrate 170 is not illustrated.

Then, as shown in FIG. 6, the first container 100 was stacked on the second container 300. A 24-well plate (purchased from Corning Incorporated) was used as the second container 300. The back surface 104b of the cellulose film 104 was in contact with the liquid culture medium 302. The 10% LCH culture medium was used as the liquid culture medium 302. The phytopathogenic fungus aqueous solution containing 1,000 spores of *Colletotrichum gloeosporioides* was added to the inside of the first container 100.

The first container 100 was left at rest at a temperature of 25 degrees Celsius for 24 hours. In other words, in the inventive example 1A, the incubation time was 24 hours.

(Detection of Fungus)

Then, the present inventors separated the first container 100 from the second container 300. Furthermore, the present inventors removed the solution contained in the first container 100 with a pipette. Subsequently, the present inventors surrounded the circumference of the first container 100 with a black 24-well plate (purchased from zell-kontakt GmbH, trade name: Imaging plate FC) to shield the first container 100 from light.

As shown in FIG. 5B and FIG. 5C, the cellulose film 104 was irradiated with ultraviolet light using an ultraviolet light source 400 (product of Panasonic, trade name: UV-EC910ZA). The interval between the ultraviolet light source 400 and the cellulose film 104 was 1.5 centimeters. An electric current of 0.1 ampere flowed for ten minutes through the ultraviolet light source 400.

Then, the present inventors brought the WST reaction liquid (100 microliters) into contact with the back surface 104*b* of the cellulose film 104. Subsequently, the first container 100 was shielded from light at a temperature of 25 degrees Celsius for one hour in such a manner that light was not incident on the cellulose film 104.

The present inventors moved the WST reaction liquid (50 microliters) which had been brought into contact with the back surface 104*b* of the cellulose film 104 to a 96-well flat-bottom transparent plate (purchased from Greiner Bio-One international GmbH). Then, the present inventors measured an absorbance of the WST reaction liquid at a wavelength of 460 nanometers using a plate reader (purchased from Tecan Japan Co., Ltd., trade name: M1000Pro).

Apart from this, as a reference, the WST reaction liquid was left at rest at a temperature of 25 degrees Celsius for one hour. Then, the absorbance of the WST-reaction liquid was measured similarly. Needless to say, the WST reaction liquid used as the reference was not brought into contact with the back surface 104*b* of the cellulose film 104. The inventive example 1A was repeated twice.

The present inventors calculated a color reaction degree in accordance with the following mathematical formula (I).

Color reaction degree=(Absorbance of the WST reaction liquid brought into contact with the back surface 104*b* of the cellulose film 104)−(Absorbance of the WST reaction liquid as the reference) (I)

The results are shown in the following Table 2.

TABLE 2

| | Absorbance of the WST reaction liquid |
|---|---|
| WST reaction liquid brought into contact with the back surface 104b (First try) | 0.428 |
| WST reaction liquid as the reference (First try) | 0.046 |
| WST reaction liquid brought into contact with the back surface 104b (Second try) | 0.308 |
| WST reaction liquid as the reference (Second try) | 0.044 |

From the above Table 2, the mean value of the color reaction degree of *Colletotrichum gloeosporioides* in the inventive example 1 is 0.32 (=((0.428−0.046)+(0.308−0.044))/2).

Inventive Example 1B

In the inventive example 1B, an experiment similar to the inventive example 1A was conducted, except that the cellulose solution had a concentration of 3% and that the cellulose film 104 had a thickness of 3.7 micrometers. The results are shown in the following Table 3.

TABLE 3

| | Absorbance of the WST reaction liquid |
|---|---|
| WST reaction liquid brought into contact with the back surface 104b (First try) | 0.361 |
| WST reaction liquid as the reference (First try) | 0.054 |
| WST reaction liquid brought into contact with the back surface 104b (Second try) | 0.257 |
| WST reaction liquid as the reference (Second try) | 0.043 |

Inventive Example 1C

In the inventive example 1C, an experiment similar to the inventive example 1A was conducted, except that a waterproof tape (purchased from Nitto Denko Corporation, trade name: 57130SB) was adhered to the whole of the back surface 104*b* of the cellulose film 104. The waterproof film prevented the fungus from growing out of the back surface 104*b* of the cellulose film 104. The results are shown in the following Table 4.

TABLE 4

|  | Absorbance of the WST reaction liquid |
| --- | --- |
| WST reaction liquid brought into contact with the back surface 104b (First try) | 0.078 |
| WST reaction liquid as the reference (First try) | 0.046 |
| WST reaction liquid brought into contact with the back surface 104b (Second try) | 0.064 |
| WST reaction liquid as the reference (Second try) | 0.044 |

Inventive Example 1 D

In the inventive example 1 D, an experiment similar to the inventive example 1A was conducted, except that the cellulose solution had a concentration of 3%, except that the cellulose film 104 had a thickness of 3.7 micrometers, and except that the waterproof tape was adhered to the whole of the back surface 104b of the cellulose film 104. The results are shown in the following Table 5.

TABLE 5

|  | Absorbance of the WST reaction liquid |
| --- | --- |
| WST reaction liquid brought into contact with the back surface 104b (First try) | 0.071 |
| WST reaction liquid as the reference (First try) | 0.054 |
| WST reaction liquid brought into contact with the back surface 104b (Second try) | 0.062 |
| WST reaction liquid as the reference (Second try) | 0.043 |

(Experiment 2)

The experiment 2 is composed of inventive examples 2A-2D. In the experiment 2, an experiment similar to the experiment 1 was conducted except for using *Fusarium avenaceum* in place of *Colletotrichum gloeosporioides*.

The results of the inventive example 2A are shown in the following Table 6.

TABLE 6

|  | Absorbance of the WST reaction liquid |
| --- | --- |
| WST reaction liquid brought into contact with the back surface 104b (First try) | 0.273 |
| WST reaction liquid as the reference (First try) | 0.046 |
| WST reaction liquid brought into contact with the back surface 104b (Second try) | 0.273 |
| WST reaction liquid as the reference (Second try) | 0.056 |

The results of the inventive example 2B are shown in the following Table 7.

TABLE 7

|  | Absorbance of the WST reaction liquid |
| --- | --- |
| WST reaction liquid brought into contact with the back surface 104b (First try) | 0.213 |
| WST reaction liquid as the reference (First try) | 0.054 |
| WST reaction liquid brought into contact with the back surface 104b (Second try) | 0.204 |

TABLE 7-continued

|  | Absorbance of the WST reaction liquid |
| --- | --- |
| WST reaction liquid as the reference (Second try) | 0.063 |

The results of the inventive example 2C are shown in the following Table 8.

TABLE 8

|  | Absorbance of the WST reaction liquid |
| --- | --- |
| WST reaction liquid brought into contact with the back surface 104b (First try) | 0.060 |
| WST reaction liquid as the reference (First try) | 0.061 |
| WST reaction liquid brought into contact with the back surface 104b (Second try) | 0.077 |
| WST reaction liquid as the reference (Second try) | 0.056 |

The results of the inventive example 2D are shown in the following Table 9.

TABLE 9

|  | Absorbance of the WST reaction liquid |
| --- | --- |
| WST reaction liquid brought into contact with the back surface 104b (First try) | 0.057 |
| WST reaction liquid as the reference (First try) | 0.062 |
| WST reaction liquid brought into contact with the back surface 104b (Second try) | 0.071 |
| WST reaction liquid as the reference (Second try) | 0.063 |

The following Table 10 shows the results of the inventive examples 1A-1D and the inventive examples 2A-2D.

TABLE 10

|  | Fungus name | Film thickness (μm) | Waterproofing tape | Color reaction degree |
| --- | --- | --- | --- | --- |
| Inventive example 1A | *Colletotrichum gloeosporioides* | 0.5 | Absent | 0.32 |
| Inventive example 1B |  | 3.7 | Absent | 0.26 |
| Inventive example 1C |  | 0.5 | Present | 0.03 |
| Inventive example 1D |  | 3.7 | Present | 0.02 |
| Inventive example 2A | *Fusarium avenaceum* | 0.5 | Absent | 0.22 |
| Inventive example 2B |  | 3.7 | Absent | 0.15 |
| Inventive example 2C |  | 0.5 | Present | 0.01 |
| Inventive example 2D |  | 3.7 | Present | 0.00 |

As is clear from Table 10, the phytopathogenic fungus which penetrated the cellulose film 104 was detected.

(Experiment 3)

With regard to *Botrytis cinerea*, which is one of phytopathogenic fungi, similarly to the case of the experiment 1, a phytopathogenic fungus aqueous solution containing spores of *Botrytis cinerea* was provided.

The experiment 3 is composed of an inventive example 3 and comparative examples 3A-3C.

Inventive Example 3

The first container 100 shown in FIG. 1 was prepared similarly to the case of the above-mentioned inventive example 1.

Next, as shown in FIG. 6, the first container 100 was stacked on the second container 300. As the second container 300 and the liquid medium 302, those similar to the case of the above-mentioned inventive example 1 were used. The phytopathogenic fungus aqueous solution containing 1,000 spores of *Botrytis cinerea* was added to the inside of the first container 100.

The first container 100 was left at rest at a temperature of 25 degrees Celsius for 40 hours.

Next, similarly to the case of the above-mentioned inventive example 1, the first container 100 was separated from the second container 300. The solution contained in the first container 100 was removed, and then, the first container 100 was shielded from light.

As shown in FIG. 5B and FIG. 5C, similarly to the case of the above-mentioned inventive example 1, the cellulose film 104 was irradiated with ultraviolet light using the ultraviolet light source 400.

Next, the WST reaction liquid (100 microliters) was brought into contact with the back surface 104b of the cellulose film 104. Subsequently, the first container 100 was shielded from light at 25 degrees Celsius for 3 hours in such a manner that the cellulose film 104 was not irradiated with light.

Next, similarly to the case of the above-mentioned inventive example 1, the absorbance of the WST reaction liquid (50 microliters) brought into contact with the back surface 104b of the cellulose film 104 was measured.

Comparative Example 3A

In the comparative example 3A, an experiment similar to the inventive example 3 was conducted, except that the cellulose solution having a concentration of 5% was used in place of the cellulose solution having a concentration of 1% and that a container in which the diameter of each of the through hole was 1 micrometer (Millipore company, trade name: Millicell PIRP 12R 48) was used in place of the container in which the diameter of each of the through hole was 3 micrometers (Millipore company, trade name: Millicell PISP 12R 48), as the container having a polyethylene terephthalate film having plural through holes on the bottom thereof, when the first container 100 in the inventive example 3 was prepared.

Comparative Example 3B

In the comparative example 3B, an experiment similar to the above-mentioned inventive example 3 was conducted, except that the cellulose film 104 was not irradiated with ultraviolet light.

Comparative Example 3C

In the comparative example 3C, an experiment similar to the above-mentioned comparative example 3A was conducted, except that the cellulose film 104 was not irradiated with ultraviolet light.

(Experiment 4)

With regard to *Passalora fulva*, which is one of phytopathogenic fungi, similarly to the case of the experiment 1, a phytopathogenic fungus aqueous solution containing spores of *Passalora fulva* was provided.

The experiment 4 is composed of an inventive example 4 and comparative examples 4A-4B.

Inventive Example 4

The first container 100 shown in FIG. 1 was prepared similarly to the case of the above-mentioned inventive example 1.

Next, as shown in FIG. 6, the first container 100 was stacked on the second container 300. As the second container 300 and the liquid medium 302, those similar to the case of the above-mentioned inventive example 1 were used. The phytopathogenic fungus aqueous solution containing 1,000 spores of *Passalora fulva* was added to the inside of the first container 100.

The first container 100 was left at rest at a temperature of 25 degrees Celsius for 120 hours.

Next, similarly to the case of the above-mentioned inventive example 1, the first container 100 was separated from the second container 300. The solution contained in the first container 100 was removed, and then, the first container 100 was shielded from light.

As shown in FIG. 5B and FIG. 5C, similarly to the case of the above-mentioned inventive example 1, the cellulose film 104 was irradiated with ultraviolet light using the ultraviolet light source 400.

Next, the WST reaction liquid (100 microliters) was brought into contact with the back surface 104b of the cellulose film 104. Subsequently, the first container 100 was shielded from light at 25 degrees Celsius for 3 hours in such a manner that the cellulose film 104 was not irradiated with light.

Next, similarly to the case of the above-mentioned inventive example 1, the absorbance of the WST reaction liquid (50 microliters) brought into contact with the back surface 104b of the cellulose film 104 was measured.

Comparative Example 4A

In the comparative example 4A, an experiment similar to the inventive example 4 was conducted, except that the cellulose solution having a concentration of 5% was used in place of the cellulose solution having a concentration of 1% and that a container in which the diameter of each of the through hole was 1 micrometer (Millipore company, trade name: Millicell PIRP 12R 48) was used in place of the container in which the diameter of each of the through hole was 3 micrometers (Millipore company, trade name: Millicell PISP 12R 48), as the container having a polyethylene terephthalate film having plural through holes on the bottom thereof, when the first container 100 in the inventive example 4 was prepared.

Comparative Example 4B

In the comparative example 4B, an experiment similar to the above-mentioned inventive example 4 was conducted, except that the cellulose film 104 was not irradiated with ultraviolet light.

(Experiment 5)

With regard to *Pseudocercospora fuligena*, which is one of phytopathogenic fungi, similarly to the case of the experiment 1, a phytopathogenic fungus aqueous solution containing spores of *Pseudocercospora fuligena* was provided.

The experiment 5 is composed of an inventive example 5 and comparative examples 5A-5B.

Inventive Example 5

The first container 100 shown in FIG. 1 was prepared similarly to the case of the above-mentioned inventive example 1.

Next, as shown in FIG. 6, the first container 100 was stacked on the second container 300. As the second container 300 and the liquid medium 302, those similar to the case of the above-mentioned inventive example 1 were used. The phytopathogenic fungus aqueous solution containing 1,000 spores of *Pseudocercospora fuligena* was added to the inside of the first container 100.

The first container 100 was left at rest at a temperature of 25 degrees Celsius for 75 hours.

Next, similarly to the case of the above-mentioned inventive example 1, the first container 100 was separated from the second container 300. The solution contained in the first container 100 was removed, and then, the first container 100 was shielded from light.

As shown in FIG. 5B and FIG. 5C, similarly to the case of the above-mentioned inventive example 1, the cellulose film 104 was irradiated with ultraviolet light using the ultraviolet light source 400.

Next, the WST reaction liquid (100 microliters) was brought into contact with the back surface 104b of the cellulose film 104. Subsequently, the first container 100 was shielded from light at 25 degrees Celsius for 1 hour in such a manner that the cellulose film 104 was not irradiated with light.

Next, similarly to the case of the above-mentioned inventive example 1, the absorbance of the WST reaction liquid (50 microliters) brought into contact with the back surface 104b of the cellulose film 104 was measured.

Comparative Example 5A

In the comparative example 5A, an experiment similar to the inventive example 5 was conducted, except that the cellulose solution having a concentration of 5% was used in place of the cellulose solution having a concentration of 1% and that a container in which the diameter of each of the through hole was 1 micrometer (Millipore company, trade name: Millicell PIRP 12R 48) was used in place of the container in which the diameter of each of the through hole was 3 micrometers (Millipore company, trade name: Millicell PISP 12R 48), as the container having a polyethylene terephthalate film having plural through holes on the bottom thereof, when the first container 100 in the inventive example 5 was prepared.

Comparative Example 5B

In the comparative example 5B, an experiment similar to the above-mentioned inventive example 5 was conducted, except that the cellulose film 104 was not irradiated with ultraviolet light.

The following Table 11 shows the results of the experiments 3-5. Note that the number of the hyphae which have penetrated in Table 11 is the result of counting the number of the hyphae which have penetrated the cellulose film 104.

TABLE 11

|  | Name of fungus | Diameter (μm) | UV treatment | Number of hyphae which have penetrated | Color reaction degree |
|---|---|---|---|---|---|
| I.E. 3 | *Botrytis cinerea* | 3 | Present | 205 | 0.08 |
| C.E. 3A |  | 1 | Present | 6 | 0.00 |
| C.E. 3B |  | 3 | Absent | 299 | 0.40 |
| C.E. 3C |  | 1 | Absent | 0 | 0.37 |
| I.E. 4 | *Passalora fulva* | 3 | Present | 58 | 0.15 |
| C.E. 4A |  | 1 | Present | 0 | 0.02 |
| C.E. 4B |  | 3 | Absent | 0 | 0.71 |
| I.E. 5 | *Pseudocercospora* | 3 | Present | 400 | 0.40 |
| C.E. 5A | *fuligena* | 1 | Present | 0 | 0.04 |
| C.E. 5B |  | 3 | Absent | 337 | 0.71 |

The color reaction degree in the experiments 3-5 is based on only the hyphae which have penetrated the cellulose film 104 in a condition where the fungi on the substrate 170 have been killed by irradiation of the ultraviolet light.

In addition, the comparative examples 3A, 4A, and 5A were conducted in a condition where it was difficult for fungi to penetrate, no or few fungi penetrated. Therefore, the fungi on the substrate 170 were killed by irradiation of the ultraviolet light, and the color reaction degrees significantly lower than those of the inventive examples 3-5 are exhibited. From the respective comparison of these comparative examples 3A, 4A, and 5A to the inventive examples 3-5, it is understood that the presence or absence of the hyphae which have penetrated can be determined by the method according to the present invention on the basis of the color reaction degree.

In addition, in the comparative examples 3B, 3C, 4B, and 5B, since the cellulose film was not irradiated with ultraviolet light, the fungi on the substrate 170 were not killed. Therefore, regardless of presence or absence of the hyphae which have penetrated, the respective color reaction degrees which are higher than the inventive examples 3-5 are exhibited. The presence or absence of the hyphae which have penetrated fails to be determined As above, from the results of the experiments 3-5, in the method according to the present invention, whether or not the test sample contains a phytopathogenic fungus is determined by that the phytopathogenic fungus which has penetrated the cellulose film give color to the fungus color reaction reagent.

INDUSTRIAL APPLICABILITY

The present invention can be used to determine easily whether or not a test sample such as agricultural water or soil contains a phytopathogenic fungus.

REFERENCE SIGNS LIST

100 First container
102 Flange
104 Cellulose film
104a Front surface
104b Back surface
170 Substrate
170a Front surface
170b Back surface
200 Test sample
202 Phytopathogenic fungus
202a Part of Phytopathogenic fungus
300 Second container
302 Liquid culture medium
304 Solid culture medium
402 Fluorescent agent having fungus color reaction reagent
500 Light source
600 Microscope

The invention claimed is:

1. A method for determining whether or not a test sample contains a phytopathogenic fungus, the method comprising:
   (a) putting the test sample on a front surface of a substrate comprising a through hole;
   wherein
   the substrate comprises a cellulose film on a back surface thereof;
   the through hole of the substrate has a cross-sectional area of not less than 7.065 square micrometers and not more than 19.625 square micrometers;
   the cellulose film has no through hole; and
   the cellulose film has a thickness of not less than 0.5 micrometers and not more than 3.7 micrometers;
   (b) leaving the test sample at rest after the step (a);
   (c) irradiating the cellulose film with ultraviolet light using an ultraviolet light source provided so as to face the front surface of the cellulose film after the step (b);
   (d) bringing a back surface of the cellulose film into contact with a fungus color reaction reagent after the step (c); and
   (e) determining that the test sample contains the phytopathogenic fungus, if a color is given to the fungus color reaction reagent.

2. The method according to claim 1, wherein the phytopathogenic fungus is a phytopathogenic mycete.

3. The method according to claim 2, wherein the phytopathogenic mycete is at least one selected from the group consisting of a *Colletotrichum* genus, a *Fusarium* genus, a *Botrytis* genus, a *Passalora* genus, and a *Pseudocercospora* genus.

4. The method according to claim 2, wherein the phytopathogenic mycete is at least one selected from the group consisting of *Colletotrichum gloeosporioides*, *Fusarium avenaceum*, *Botrytis cinerea*, *Passalora fulva*, and *Pseudocercospora fuligena*.

5. The method according to claim 1, wherein the phytopathogenic fungus is a phytopathogenic oomycete.

6. The method according to claim 1, further comprising:
a step of supplying a culture medium to the test sample before the step (b).

7. The method according to claim 6, wherein the culture medium is a liquid culture medium.

8. The method according to claim 6, wherein the culture medium is a solid culture medium.

9. The method according to claim 1, wherein the test sample is left at rest while the back surface of the cellulose film is in contact with the culture medium in the step (b).

10. The method according to claim 9, wherein the culture medium is a liquid culture medium.

11. The method according to claim 9, wherein the culture medium is a solid culture medium.

12. The method according to claim 1, wherein the test sample is solid.

13. The method according to claim 12, wherein the solid test sample is at least one selected from the group consisting of soil and a crushed plant.

14. The method according to claim 1, wherein the test sample is liquid.

15. The method according to claim 14, wherein the liquid test sample is at least one selected from the group consisting of agricultural water, a liquid used for hydroponic culture, a liquid used for washing a plant, a liquid extracted from a plant, a liquid used for washing an agricultural material, and a liquid used for washing clothing or a shoe.

* * * * *